US 6,640,805 B2
(12) United States Patent
Castro et al.

(10) Patent No.: US 6,640,805 B2
(45) Date of Patent: Nov. 4, 2003

(54) METERING VALVE FOR A METERED DOSE INHALER HAVING IMPROVED FLOW

(75) Inventors: Gustavo H. Castro, Cottage Grove, MN (US); Thomas Herdtle, Inver Grove Heights, MN (US); Cathleen M. Arsenault, Hugo, MN (US); Antony J. Davis, Hugglescote (GB)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/100,641

(22) Filed: Mar. 19, 2002

(65) Prior Publication Data

US 2002/0134376 A1 Sep. 26, 2002

Related U.S. Application Data

(60) Provisional application No. 60/278,890, filed on Mar. 26, 2001.

(51) Int. Cl.$^7$ ............................................. A61M 11/00
(52) U.S. Cl. ........................ 128/200.23; 128/200.14; 222/1; 222/394; 222/402.1
(58) Field of Search ..................... 128/200.23, 200.13, 128/200.14; 222/402.1, 394, 372, 402.19, 402.16, 402.2

(56) References Cited

U.S. PATENT DOCUMENTS

| 3,169,677 | A | | 2/1965 | Focht |
| 4,427,137 | A | * | 1/1984 | Dubini ................... 222/402.2 |
| 4,592,700 | A | * | 6/1986 | Toguchi et al. ............. 415/225 |
| 4,819,834 | A | | 4/1989 | Thiel |
| 5,104,233 | A | * | 4/1992 | Kojima ...................... 366/339 |
| 5,169,038 | A | * | 12/1992 | Di Giovanni ............ 222/402.2 |
| 5,400,920 | A | | 3/1995 | Barnhart |
| 5,477,992 | A | | 12/1995 | Jinks et al. |
| 5,632,421 | A | * | 5/1997 | Colombo .................. 222/402.2 |
| 5,772,085 | A | | 6/1998 | Bryant et al. |
| 5,836,299 | A | * | 11/1998 | Kwon .................... 128/200.23 |
| 5,921,447 | A | | 7/1999 | Barger et al. |
| 5,938,085 | A | | 8/1999 | Conroy et al. |

FOREIGN PATENT DOCUMENTS

| EP | 0 143 577 B1 | 7/1989 |
| FR | 1.461.685 | 2/1966 |
| GB | 798683 | 7/1958 |
| GB | 2 086 845 A | 5/1982 |
| GB | 2 004 526 B | 7/1982 |
| GB | 2 206 099 A | 12/1988 |
| GB | 2 312 418 A | 10/1997 |

* cited by examiner

Primary Examiner—Weilun Lo
Assistant Examiner—Michael G. Mendoza
(74) Attorney, Agent, or Firm—Christopher D. Gram; Ted K. Ringsred; Robert W. Sprague (57) ABSTRACT

A novel metering valve having improved flow for delivery of an aerosol formulation is disclosed. Methods of delivering an aerosol formulation using a device comprising the novel metering valve are also disclosed.

30 Claims, 10 Drawing Sheets

METERING VALVE FOR A METERED DOSE INHALER HAVING IMPROVED FLOW

This application claims the benefit of U.S. provisional patent application Ser. No. 60/278,890, filed Mar. 26, 2001.

BACKGROUND

Metering valves are a common means by which aerosols are dispensed from aerosol containers. Metering valves are particularly useful for administering medicinal formulations that include a liquefied gas propellant and are delivered to a patient in an aerosol.

When administering medicinal formulations, a dose of formulation sufficient to produce the desired physiological response is delivered to the patient. The proper, predetermined amount of the formulation must be dispensed to the patient in each successive dose. Thus, any dispensing system must be able to dispense doses of the medicinal formulation accurately and reliably to help assure the safety and efficacy of the treatment.

Metering valves have been developed to provide control over the dispensing of medicinal aerosol formulations. A metering valve may be used to regulate the volume of a medicinal formulation passing from a container to a metering chamber, which defines the maximum amount of the formulation that will be dispensed as the next dose. The precise dosage metered by the metering chamber may be dependent, in part, upon the physical conditions under which the medicinal formulation is permitted to fill the metering chamber. Reliable and controllable flow of the medicinal formulation into the metering chamber may contribute to the accuracy and/or precision of the metering of successive doses of the formulation. Thus, reliable and controllable flow of the medicinal formulation into the metering chamber may improve performance of the metering valve and, therefore, may be highly desirable.

In some metering valves, the metering chamber fills with the medicinal formulation prior to the patient actuating the valve stem and thereby releasing the dose. The metering chamber is refilled with formulation after dispensing one dose so that the metering valve is ready to discharge the next dose. Consequently, the metering chamber contains formulation at all times except for the brief time during which the valve stem is depressed by the user to discharge a dose. Also, the passageways through which the formulation must flow to reach the metering chamber are often narrow and tortuous. As a result, metering valves configured in this way have a number of disadvantages resulting in, for example, erratic dosing due to loss of prime, i.e., the occurrence of vapor or air voids in the metered volume, which may leading to a shortfall in the volume of dose being metered by the valve.

In other metering valves, the metering chamber does not materialize unless and until the valve stem is actuated. Actuation of these valve stems can be divided into a filling stage and a discharge stage. The filling stage begins as the valve stem is depressed during actuation. The action of depressing the valve stem causes the formation of a transient metering chamber. As the valve stem is depressed, the transient metering chamber expands and formulation enters the metering chamber. As displacement of the valve stem continues, a stage is reached at which filling of the transient metering chamber stops. Eventually, displacement of the valve stem continues to the discharge stage, in which the metered formulation is discharged. In these valves, a single actuation thus causes rapid filling of the transient metering chamber followed by discharge of the formulation to the patient. Thus, the metered formulation does not reside for any appreciable amount of time in the metering chamber.

While a metering valve having a transient metering chamber provides advantages over other types of metering valves for the delivery of aerosol formulations, the flow of formulation from the container to the metering chamber may be disrupted. When this happens, formulation may be delivered in inconsistent or inaccurate doses.

What is needed is a valve stem for a metered dose inhaler that improves flow of formulation into the metering chamber, thereby providing consistent, accurate, dosages of formulation, even when actuated rapidly.

SUMMARY

It has been determined that one cause of disrupted flow of formulation may be due to the design of the valve stem in the metering valve. A seal typically isolates the metering chamber from the aerosol container once the correct volume of formulation has been metered. To accomplish this, the seal must occlude the flow path, through which formulation must pass in order to fill the metering chamber, as the valve stem is depressed beyond the filling stage. As used herein, occlude refers to at least a partial closing off of an opening by a seal, gasket, or diaphragm. In certain metering valves, the passageways leading from the container to the metering chamber can begin to become occluded well before the formulation has completed filling the metering chamber. This effectively begins to cut off flow of formulation into the metering chamber while the valve stem is still in the filling stage of actuation.

Also, the design of the valve stem may cause regions of recirculation or localized low pressure to develop in the flow of formulation into the metering chamber. Such low pressure regions can lead to incomplete metering of the formulation by allowing bubbles to form in the metered volume, particularly when the patient actuates the valve rapidly or rapid actuation occurs due to the mechanism of a breath actuated device.

The present invention provides a valve stem for a metered dose inhaler that improves the flow of formulation into the metering chamber. The novel stem design has a short, but circumferentially widened channel opening that, in many embodiments, enhances the flow of formulation into the metering chamber. Accordingly, the present invention provides an aerosol valve stem including a body that includes a body wall defining an internal chamber; at least one inlet port through the body wall in fluid communication with the internal chamber; a channel opening in the body wall having a height and a width wherein the width is greater than the height; and at least one channel providing fluid communication between the internal chamber and the channel opening.

In some embodiments, the valve stem may include a plurality of channel openings in the body wall. In these embodiments, the plurality of channel openings may define a cumulative width that is greater than the height of the channel openings.

In another aspect, the present invention provides a method of delivering an aerosol dose of medicine including providing an inhaler that includes an aerosol valve stem including: a body that includes a body wall defining an internal chamber, at least one inlet port through the body wall in fluid communication with the internal chamber, a channel opening in the body wall having a height and a width wherein the width is greater than the height, at least one channel providing fluid communication between the internal chamber and the channel opening; providing a formulation of aerosol medicine contained within the inhaler; and actuating the inhaler.

In yet another aspect the present invention provides a metering valve that includes a housing that includes an internal chamber defined by one or more chamber walls, the internal chamber comprising an outlet aperture; a diaphragm positioned at the outlet aperture and in sealing engagement with at least a portion of the housing; a metering gasket in sealing engagement with one or more chamber walls; a valve stem including: i) a body that comprises a body wall defining an internal chamber, ii) at least one inlet port through the body wall in fluid communication with the internal chamber, iii) a channel opening in the body wall having a height and a width wherein the width is greater than the height, and iv) at least one channel providing fluid communication between the internal chamber and the channel opening, wherein the valve stem passes through the aperture in slidable sealing engagement with both of the diaphragm and the metering gasket; and an annular space having a width defined by a distance between the chamber wall and the valve stem.

In some embodiments, the valve stem may include a plurality of channel openings in the body wall. In these embodiments, the plurality of channel openings may define a cumulative width that is greater than the height of the channel openings. In certain embodiments, the height of at least one channel opening may be from about 1 to about 5 times the width of the annular space.

DETAILED DESCRIPTION OF THE INVENTION

The following description is set forth in terms of aerosol metering valves used to dispense an aerosol formulation from an aerosol container. However, the metering valves and methods of the present invention have application to the delivery of virtually any pressurized fluid in an accurate, metered dose. In particular, the metering valves described herein are useful for dispensing medicinal aerosol formulations.

When used to dispense medicinal aerosol formulations, the metering valves of the present invention may be used to administer virtually any aerosol formulation of drug into a body cavity of a patient, such as the mouth, nose, anus, vagina, ears, or onto the eyes or any skin area of the patient. However, the present invention is not limited to medicinal applications and may be used wherever a precise amount of material from a pressurized fluid is to be delivered to a given region.

Figure 1:
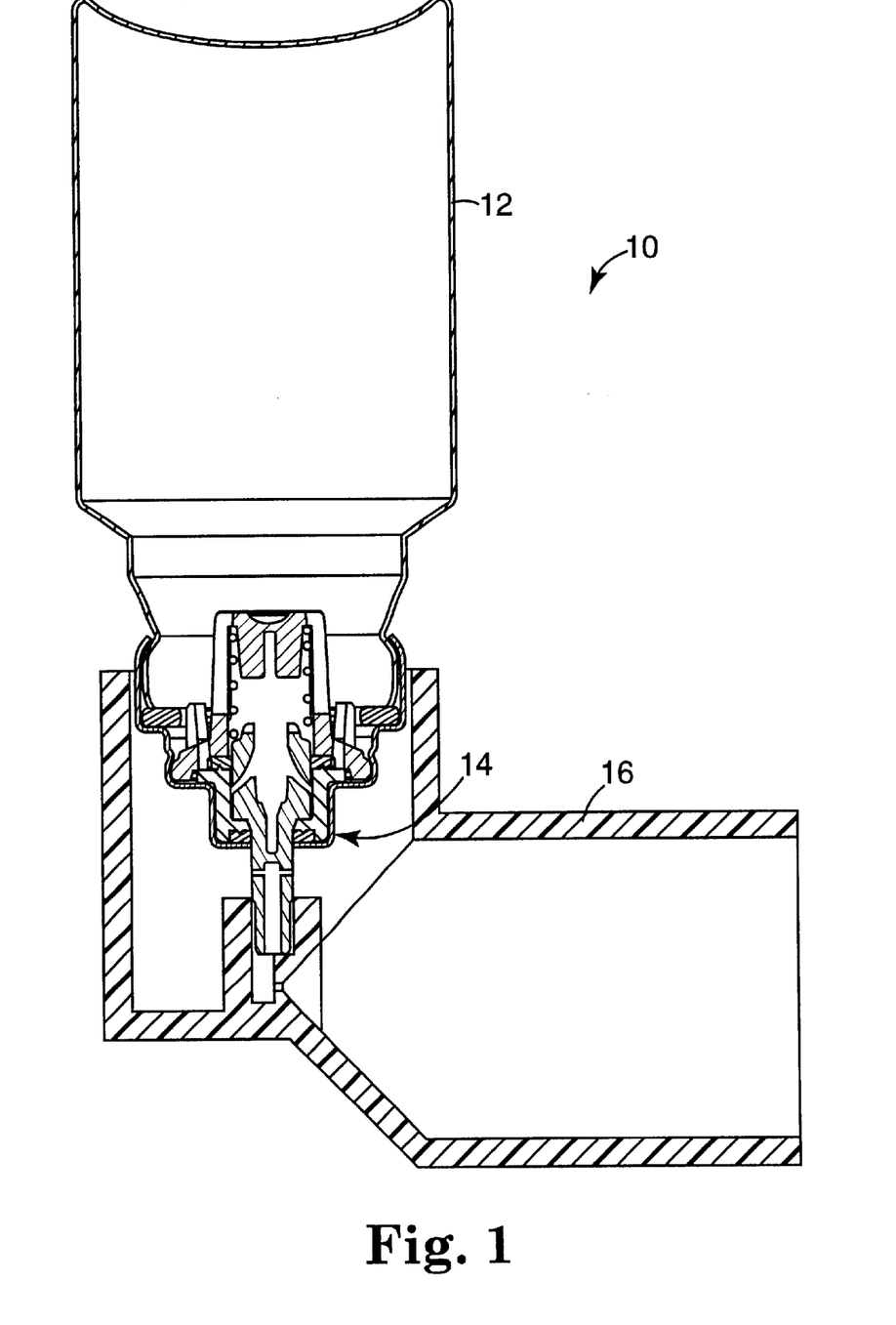
FIG. 1 is a cross-sectional view of a metered dose inhaler including the aerosol valve of the present invention.

Referring to FIG. 1, an aerosol dispensing apparatus, generally designated as 10, is illustrated that incorporates one embodiment of a metering valve 14 in accordance with the present invention. The top end of the metering valve 14 is crimped around the end of a conventional aerosol container 12, while a conventional discharge piece 16 is mounted around the bottom of the metering valve 14. Thus, aerosol formulation is dispensed downwardly from the aerosol container 12, through the metering valve 14, then through the discharge piece 16 where it is delivered to a patient. The discharge piece 16 directs the aerosol formulation toward the body cavity or skin area to which the formulation is to be delivered. The configuration of the discharge piece 16 depends upon the application for the aerosol. For example, discharge piece 16 may be a mouthpiece that can be inserted into the patient's mouth, thereby providing oral administration of the aerosol formulation. The aerosol-dispensing device shown in FIG. 1 is merely one example of how a metering valve according to the present invention can be incorporated into a dispensing apparatus.

In each of FIGS. 2–5, a metering valve is shown in isolation for ease of illustration. However, the metering valves shown in these figures may be combined with an aerosol container 12, discharge piece 16, or both, as shown in FIG. 1.

Figure 2:
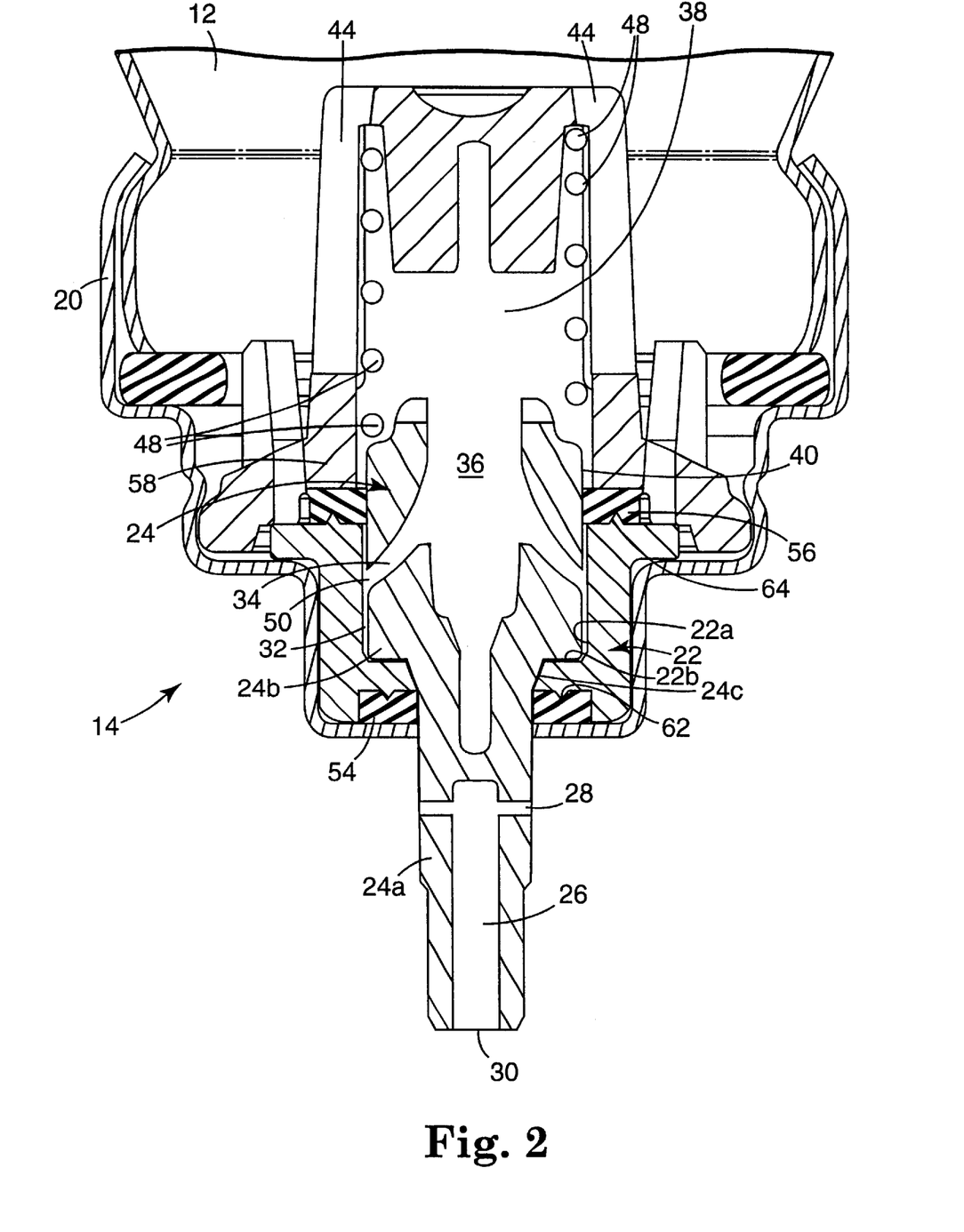
FIG. 2 is an enlarged cross-sectional view of the aerosol valve of the present invention in the resting position.

Referring to FIG. 2, the metering valve 14 is shown in the resting position. The metering valve 14 includes a housing 20 that serves to house the various components of the metering valve 14. The top portion of the housing 20 attaches to the aerosol container 12 (as shown in FIG. 1). A valve body 22 is seated within the valve housing 20 and in turn provides a housing for a valve stem 24.

The metering valve 14 may include a spring cage 58 defining an interior chamber 38, a portion of which is occupied by the valve stem 24. One or more inlets 44 provide open and unrestricted fluid communication between the interior chamber 38 and the aerosol container 12.

The valve stem 24 includes two portions, identified as 24a and 24b. The external portion of the valve stem 24a is that portion of the valve stem 24 that is positioned outside the valve housing 20 while the valve stem 24 is in the resting position shown in FIG. 2. During actuation of the valve stem 24, however, at least some of the external valve stem 24a is displaced inwardly with respect to the metering valve 14, as described more fully below, so that a portion of the external valve stem 24a is transiently positioned inside the valve housing 20. The internal valve stem 24b is that portion of the valve stem 24 that is positioned within the valve housing 20 throughout actuation of the valve stem 24.

The external valve stem 24a includes a passageway through which a metered dose of formulation is discharged, as will be described more fully below. The passageway may include one or more side holes 28, a discharge passageway 26 and a discharge opening 30.

The internal valve stem 24b may be configured to have substantially the same shape as, but to be slightly smaller than, the surrounding wall of the valve body 22a. Thus, a narrow annular space 32 may be formed between the valve body wall 22a and the internal valve stem 24b. In certain embodiments in which the valve stem 24 and the valve body wall 22a are both circular in cross-section, the narrow annular space 32 may form a ring. However, the valve stem 24 and valve body wall 22a, and therefore the narrow annular space 32, may be any suitable shape. The internal valve stem 24b includes an interior space 36 defined by the walls of the valve stem 24. One or more channels 34 are formed in the walls of the internal valve stem 24b and provide fluid communication between the interior space 36 and the narrow annular space 32 through one or more channel openings 50.

In the resting position shown in FIG. 2, the internal valve stem 24b fits concentrically inside the valve body 22 and provides sufficient clearance for the narrow annular space 32. Accordingly, only a small percentage of the metering chamber volume is present in the metering valve 14 while it is in the resting position shown in FIG. 2. As will be described in greater detail below, when the valve stem 24 is actuated, the valve stem 24 is displaced into the interior chamber 38 of the metering valve 14 and a space is created between the internal valve stem 24b and the floor of the valve body 22b. The space thus created is the metering chamber 60, as shown in FIG. 3.

In the embodiment shown in FIG. 2, a spring 48 is provided within the interior chamber 38 of the metering valve. The spring 48 serves to bias the valve stem 24 toward the resting position shown in FIG. 2. However, any suitable means for biasing the valve stem 24 into the resting position shown in FIG. 2 may be used in connection with the present invention.

The metering valve 14 also includes at least two annular gaskets, the housing gasket 54 and the metering gasket 56. The housing gasket 54 is positioned between the valve housing 20, the valve body 22 and the valve stem 24, as shown in FIG. 2. The housing gasket 54 isolates the formulation in the aerosol container 12 from the exterior of the valve by forming two fluid tight seals: 1) an annular seal between the housing gasket 54 and the valve stem 24 where the valve stem extends out of the valve housing, and 2) a compressive planar or face seal between the housing gasket 54 and the housing 20. The latter seal may be effected either with or without a sealing bead 62 on either the valve body 22 or the housing 20.

Figure 3:
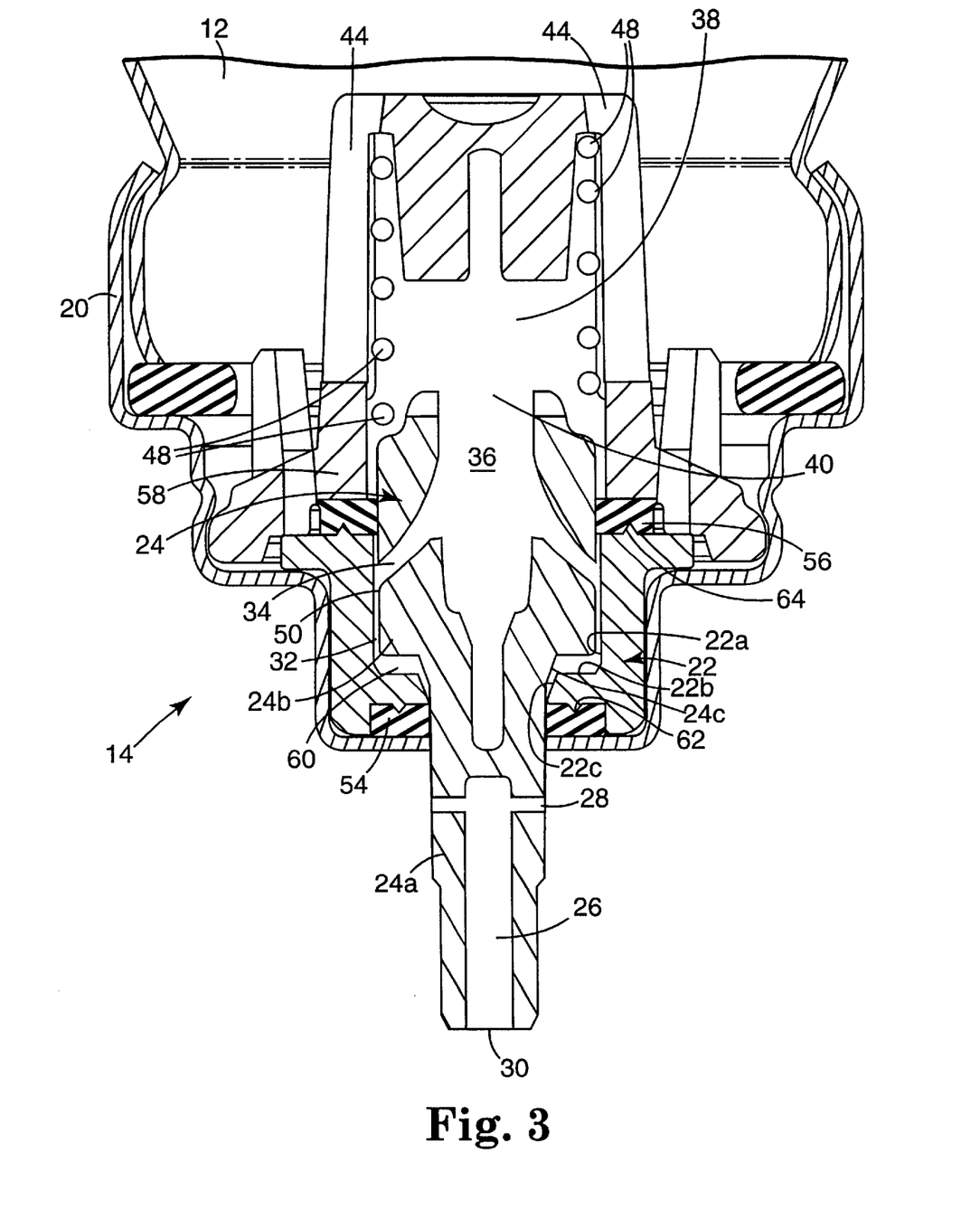
FIG. 3 is an enlarged cross-sectional view of the aerosol valve of the present invention during the filling stage of valve stem actuation.
Figure 5:
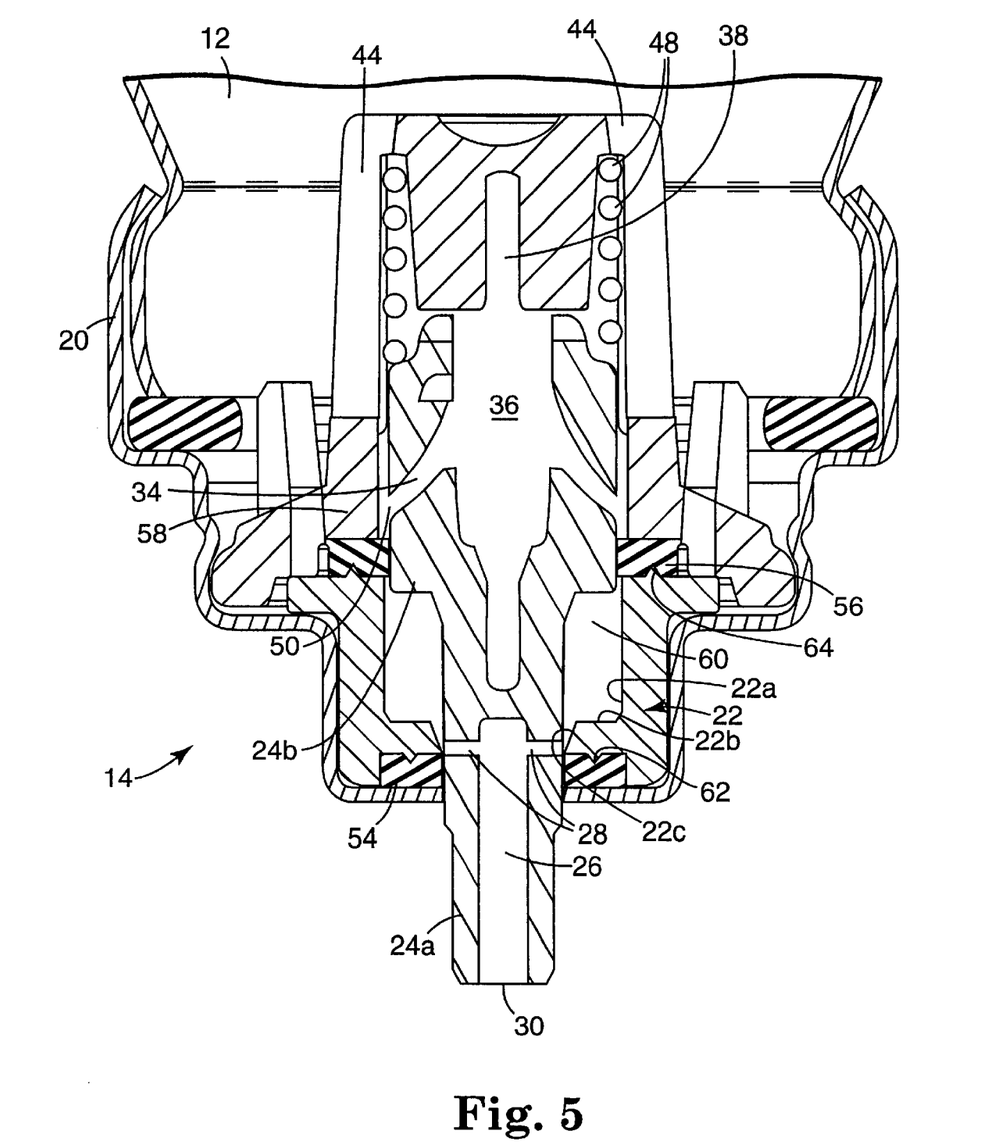
FIG. 5 is an enlarged cross-sectional view of the aerosol valve of the present invention during the discharge stage of valve stem actuation.
Figure 6A:
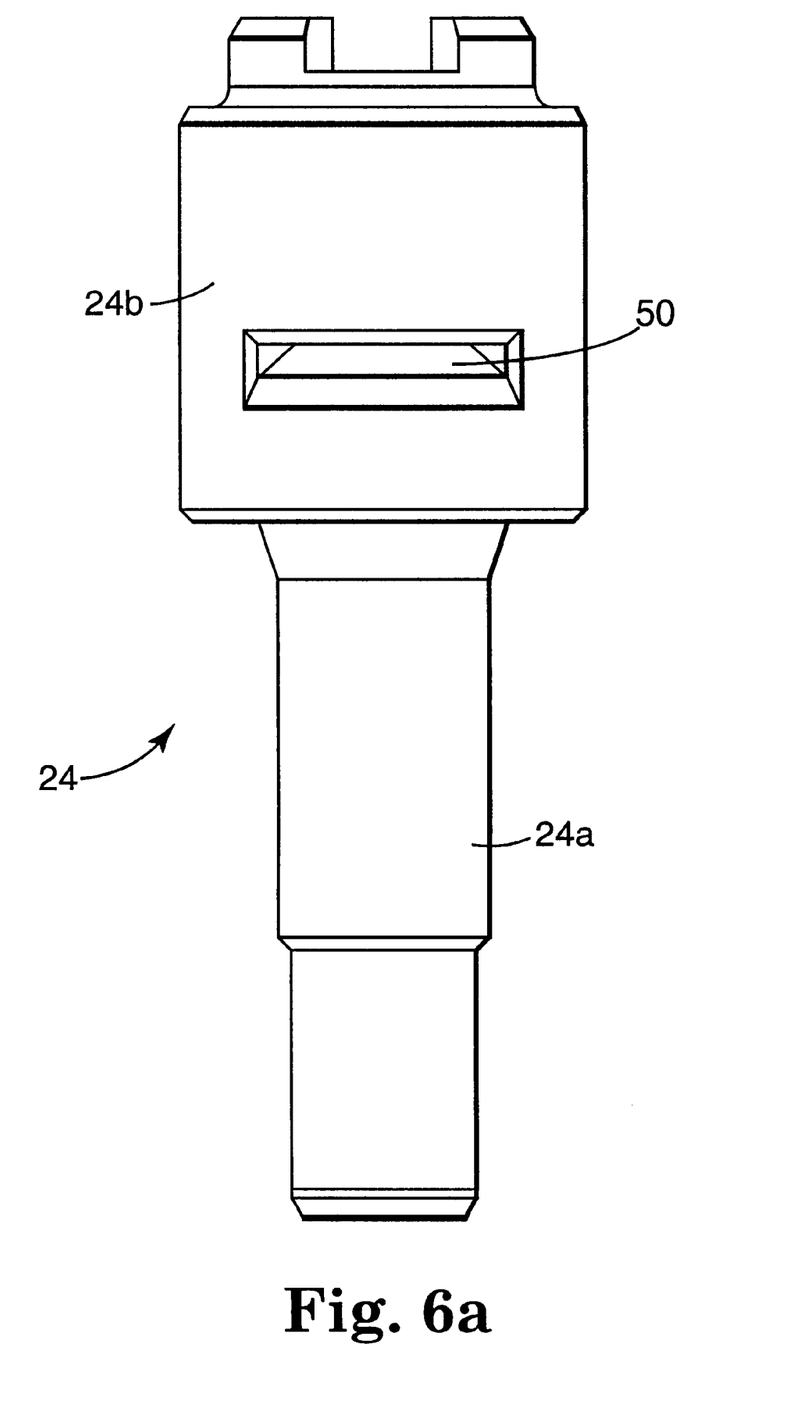
FIG. 6a is a side view of an alternative embodiment of the aerosol valve stem of the present invention.
Figure 6B:
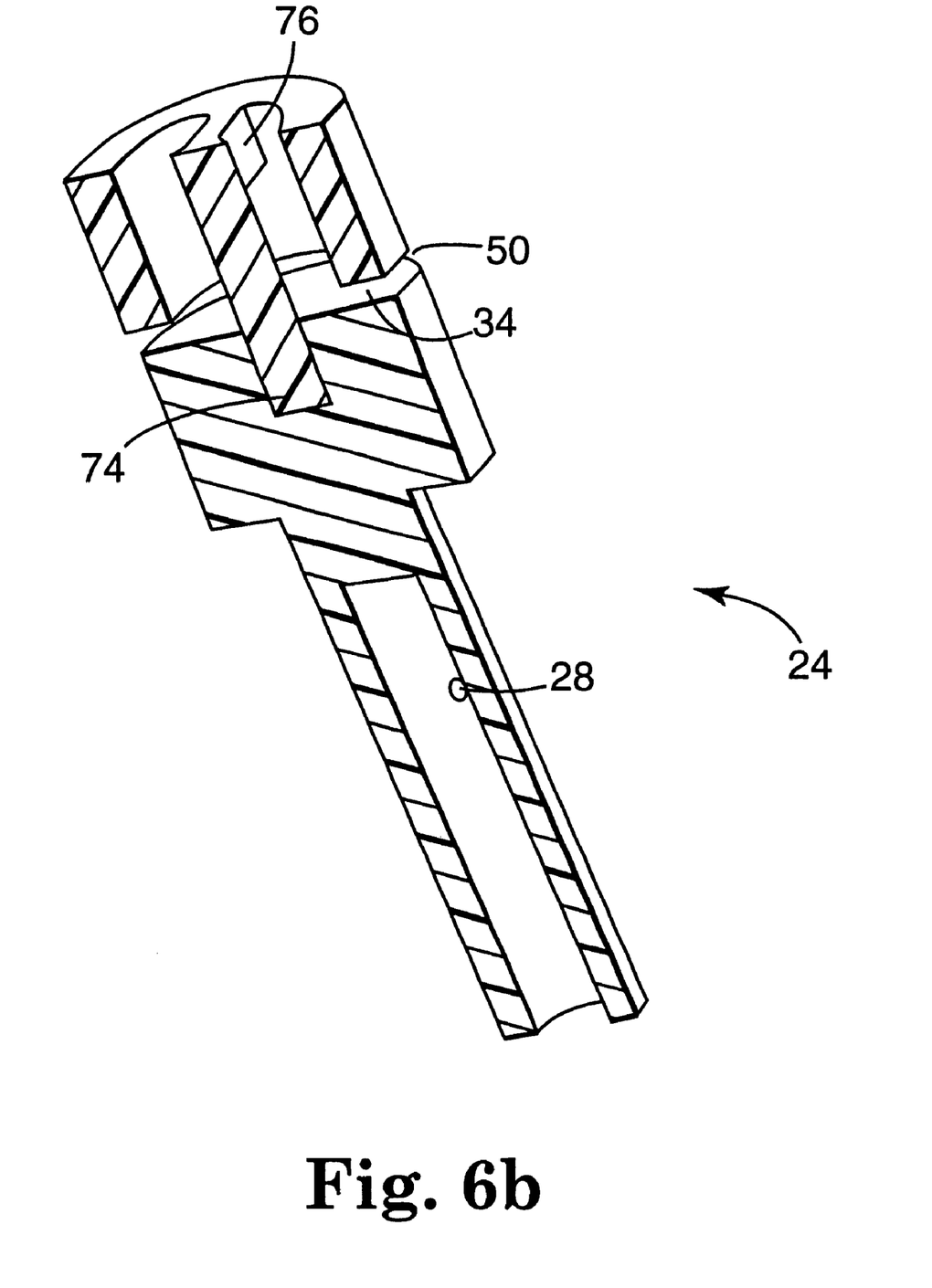
FIG. 6b is a view of a half section of an alternative embodiment of the aerosol valve stem of the present invention.

The valve body 22 may include an angled shoulder 22c, which is best seen in FIG. 3 and is designed to support the housing gasket 54 near the valve stem 24 while functioning to direct the flow of formulation out of the metering chamber 60 during the discharge stage shown in FIG. 5. The valve stem 24 may include an angled shoulder 24c designed to match the profile of the valve body 22, thereby minimizing the amount of formulation present in the metering chamber 60 in the resting position shown in FIG. 2.

Figure 4:
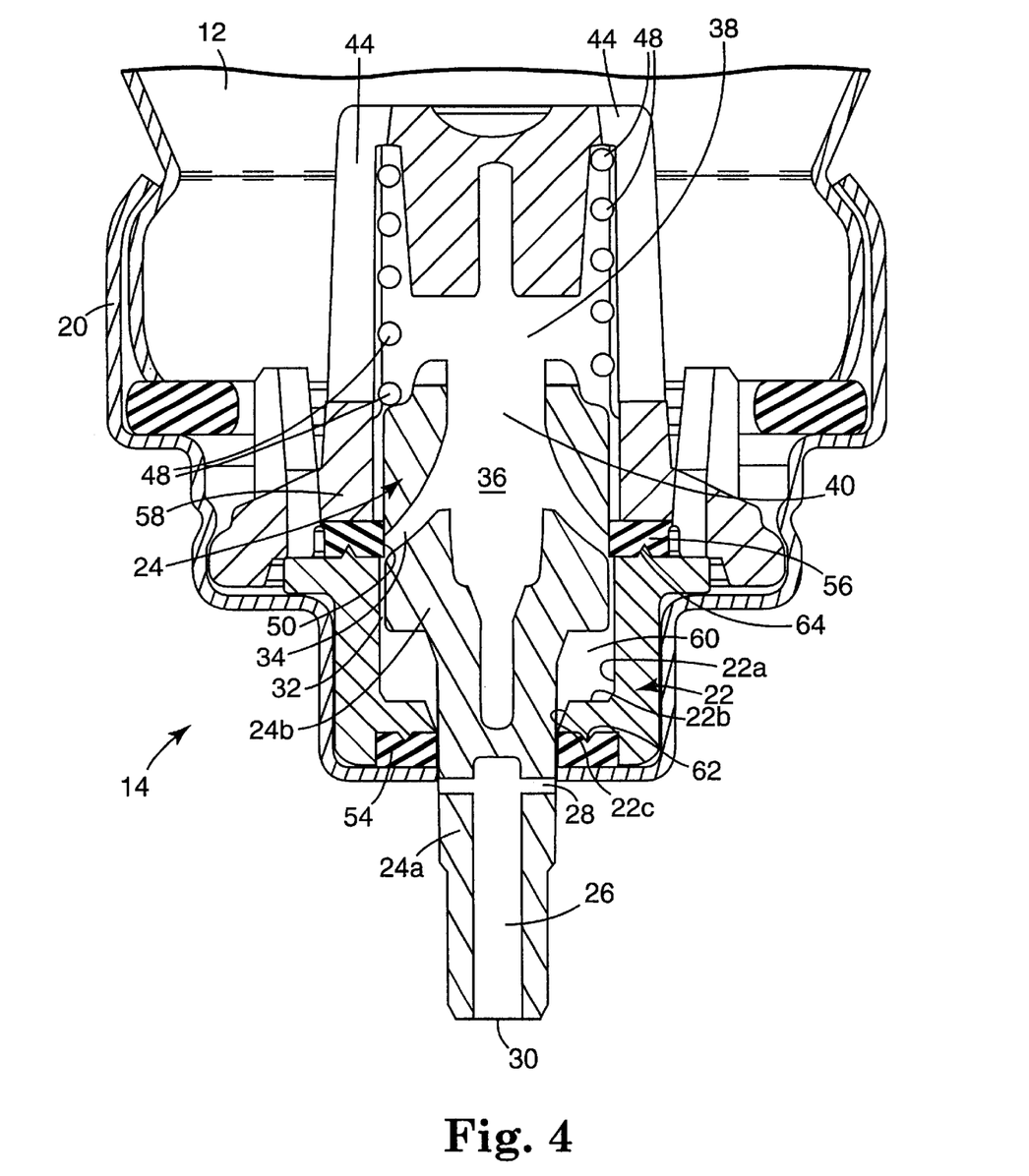
FIG. 4 is an enlarged cross-sectional view of the aerosol valve of the present invention in the filled stage of valve stem actuation.

The metering gasket 56 may be positioned between the valve body 22, the spring cage 58, and the internal part of the valve stem 24b. The metering gasket 56 transiently isolates the formulation in the metering chamber 60 from the aerosol container 12, as shown in FIGS. 4 and 5, by forming two fluid tight seals: 1) an annular seal between the metering gasket 56 and the internal part of the valve stem 24b, and 2) a compressive planar or face seal between the metering gasket 56 and the valve body 22. The latter seal may be effected either with or without a sealing bead 64 on either the valve body 22 or the spring cage 58. The metering gasket 56 provides a means for terminating the flow of formulation from the aerosol container 12 to the metering chamber 60 during actuation of the valve stem 24, as will be described in more detail below.

The operation of the metering valve 14 shown in FIG. 2 is illustrated in FIGS. 3, 4 and 5. The figures illustrate the stages of operation of the metering valve 14 and the corresponding relative positions of the valve components as a patient actuates the valve stem 24, thereby releasing a dose of aerosol formulation. FIG. 3 shows the metering valve 14 in the filling stage, FIG. 4 shows the metering valve 14 in the filled stage, and FIG. 5 shows the metering valve 14 in the discharge stage.

FIG. 3 illustrates the filling stage of the metering valve 14. The valve stem 24 has been displaced inwardly into the interior chamber 38 against the compressive force of the spring 48. As the valve stem 24 is displaced inwardly, the proximal end of the external stem 24a enters the valve housing 20 such that an annular space, the metering chamber 60, is formed between the valve body 22 and the valve stem 24. The volume of the metering chamber 60 increases as the valve stem is displaced. Displacement of the valve stem 24 typically continues until the valve stem 24 reaches a "filled" position, depicted in FIG. 4.

The aerosol formulation enters the metering chamber 60 in the following manner. Formulation from the aerosol container 12 passes through the one or more metering valve inlets 44 and into the interior chamber 38 of the metering valve. From the interior chamber 38, the formulation passes through the valve stem inlet port 40 and enters the valve stem interior space 36. Formulation then passes through one or more channels 34, one or more channel openings 50 and the narrow annular space 32, into the metering chamber 60. Consequently, as the valve stem 24 is moved from the resting position shown in FIG. 2 to the filling stage shown in FIG. 3, aerosol formulation passes from the aerosol container 12 to the metering chamber 60 immediately upon actuation of the valve stem 24. Formulation continues to fill the metering chamber 60 until the metering valve 14 reaches the filled stage depicted in FIG. 4.

FIG. 4 illustrates the metering valve 14 in the filled stage. The flow path of formulation from the aerosol container 12 to the metering chamber 60 becomes occluded as the metering gasket 56 moves past the channel opening 50. Ultimately, the channel opening 50 is fully occluded by the metering gasket 56, as shown in FIG. 4, and the flow of formulation into the metering chamber 60 is cut off, thereby concluding filling of the metering chamber 60.

Upon further actuation, the metering gasket 56 forms a fluid seal around the valve stem 24 that prevents any additional flow of formulation to the metering chamber 60. At this stage, the metered dose of formulation is isolated and ready for discharge from the metering chamber 60 and delivery to the patient. The dimensions of the valve body 22, valve stem 24 and other valve components determine the volume of the metering chamber 60 in the filled position depicted in FIG. 4. The valve body 22, valve stem 24 and other valve components may be designed to permit largely unimpeded flow of formulation during the filling stage while preventing unintended continuous discharge of formulation subject to the dimension tolerances of the valve components.

FIG. 5 depicts the metering valve 14 in the discharge stage of actuation. In order to discharge the metered dose of aerosol formulation from the metering chamber 60, the valve stem 24 may be further actuated to the position illustrated in FIG. 5. The distance traveled by the valve stem 24 between FIG. 4 and FIG. 5 may result in an expansion of the metering chamber volume without adding to the metered dose of formulation because of the seal formed between the metering gasket 56 and the valve stem 24, described above. The extra travel ensures that the metering gasket 56 is sealed against the valve stem 24 before the one or more side holes 28 enter the metering chamber 60. This extra travel thus serves to allow for dimensional variations in the valve components.

As the valve stem 24 is fully actuated, the one or more side holes 28 of the discharge passageway 26 pass through the housing gasket 54 and come into fluid communication with the metering chamber 60. That fluid communication allows the aerosol formulation within the metering chamber 60 to be released into the one or more side holes 28 and the formulation thus passes through the discharge passageway 26 and out of the discharge opening 30, thereby delivering the metered dose of aerosol formulation to the patient or other desired area.

During the discharge of the aerosol formulation from the metering chamber 60 as shown in FIG. 5, the metering gasket 56 continues to prevent the passage of additional bulk formulation from the aerosol container 12 to the metering chamber 60. After the dose of aerosol formulation is discharged, the patient releases the valve stem 24, which returns to its original resting position depicted in FIG. 2 by the biasing action of the spring 48.

The successive stages of valve stem actuation depicted in FIGS. 2, 3, 4 and 5 are all accomplished during the brief duration of actuation of the valve stem 24. Accordingly, formation, filling and emptying of the metering chamber 60 occurs rapidly. Only a small percentage of a dose of formulation resides in the metering chamber 60 between discharges, and the metering chamber 60 contains a fully metered dose of formulation only for a brief moment immediately prior to discharge of the dose from the metering chamber 60. Subsequent release of the valve stem by the patient allows the valve to return from the position depicted in FIG. 5 to that depicted in FIG. 2.

Because the valve body 22, valve stem 24 and other valve components together define the volume of the metering chamber 60, the metering valve components may be designed to form a metering chamber 60 having an appropriate metering volume for any desired application. Furthermore, metering valves having different capacities may be manufactured by, for example, altering the relative position of the channels 34 and channel opening 50 along the wall of the internal valve stem 24*b*. The volume of the metering chamber 60 at any moment is defined, in part, by the extent to which the valve stem 24 is displaced inwardly with respect to the metering valve 14.

The volume of the metering chamber 60 at the moment that the metering gasket 56 fully occludes the channel opening 50 defines the filling capacity of the metering chamber 60. Therefore, a metering valve in which the metering gasket 56 fully occludes the channel opening 50 relatively early in the displacement of the valve stem 24 will have a smaller filling capacity than a metering valve in which the metering gasket 56 fully occludes the channel opening 50 relatively late in displacement of the valve stem 24.

The channel opening 50 is defined by an axial dimension and a circumferential dimension as shown in FIG. 6*a*. As used herein, the axial dimension, or height, is the dimension parallel to the direction of displacement of the valve stem 24 during actuation. As used herein, the circumferential dimension, or width, is the dimension parallel to the circumference of the valve stem 24.

In one embodiment, at least one channel opening 50 has a cross-sectional width that is greater than its height, thereby constituting a wide, short channel opening 50. Certain embodiments of the present invention have a channel opening having a height of about 0.25 mm, some have a channel opening with a height of about 0.5 mm, and other embodiments may have a channel opening having any height ranging from about 0.01 mm to about 1.0 mm. Embodiments having a channel opening having a height from about 0.1 mm to about 0.8 mm have been identified as being particularly useful.

Certain embodiments of the present invention may have multiple channel openings 50. In such embodiments, the multiple channel openings may form a discontinuous functional equivalent of the channel opening 50 of the present invention even though no individual channel opening has a width greater than its height. In such an arrangement, the sum of the channel opening widths may define a cumulative width. Such embodiments having multiple channel openings 50 that define a cumulative circumferential width that is greater than the height of the openings are included in the scope of the present invention.

Certain other embodiments may have a single channel opening 50 that completely encircles the valve stem 24. In these embodiments, the width of the channel opening 50 essentially equals the circumference of the valve stem 24. An example of such an embodiment is depicted in FIG. 6*b*, which shows a view of a half section of a valve stem 24. While the channel opening 50 completely encircles the valve stem 24, one or more internal supports 76 join two halves of the valve stem. Sophisticated internal geometries may be manufactured by forming the valve stem 24 as two separate components that can be joined together. The components may be joined by any suitable means such as press-fitting or crimping, for example. In the embodiment shown in FIG. 6*b*, a lug 74 on the upper part of the valve stem 24 fits into a corresponding hole in the lower part of the valve stem 24.

A short channel opening height maximizes the proportion of the displacement of the valve stem 24 during actuation before the metering gasket 56 begins to occlude the channel opening 50. Thus, nearly all of the formulation enters the metering chamber 60 via steady flow before the channel opening 50 begins to be fully occluded by the metering gasket 56. This may reduce the potential effects of actuation speed with respect to filling performance. A channel opening 50 covering a large portion of the circumference of the valve stem 24 allows a large cross-sectional area for filling the annular space 32, thereby increasing the reliability and precision of the metering of the formulation. A channel opening having the combination of a wide circumference and short height may provide a desirable balance between maximizing the cross-sectional surface area of the channel opening and also maximizing the proportion of the distance the valve stem 24 travels before the channel opening 50 begins to become occluded by the metering gasket 56.

The relationship between height of the channel opening 50 and the width of the narrow annular space 32 also may influence the filling characteristics of the metering valve 14. Generally, a channel opening height of about one to about five times the width of the narrow annular space 32 permits steady flow of the formulation into the metering chamber 60 until approximately one half of the channel opening 50 is occluded by the metering gasket 56. Certain embodiments of the present invention include a channel opening height that is about three times the width of the annular space 32.

A channel opening height of greater than about five times the width of the annular space 32 may cause recirculation of flow as the metering chamber 60 fills. As used herein, recirculation refers to flow circulating or flowing back against the general direction of the flow path in a localized region within a moving fluid. Recirculating formulation may interrupt the steady flow of formulation, at least in the vicinity of the recirculating flow. This may result in at least a temporary decrease in the effective cross-sectional area of the channel opening 50 available to conduct flow of formulation, thereby reducing the rate at which formulation is allowed to flow into the metering chamber 60.

Figure 7:
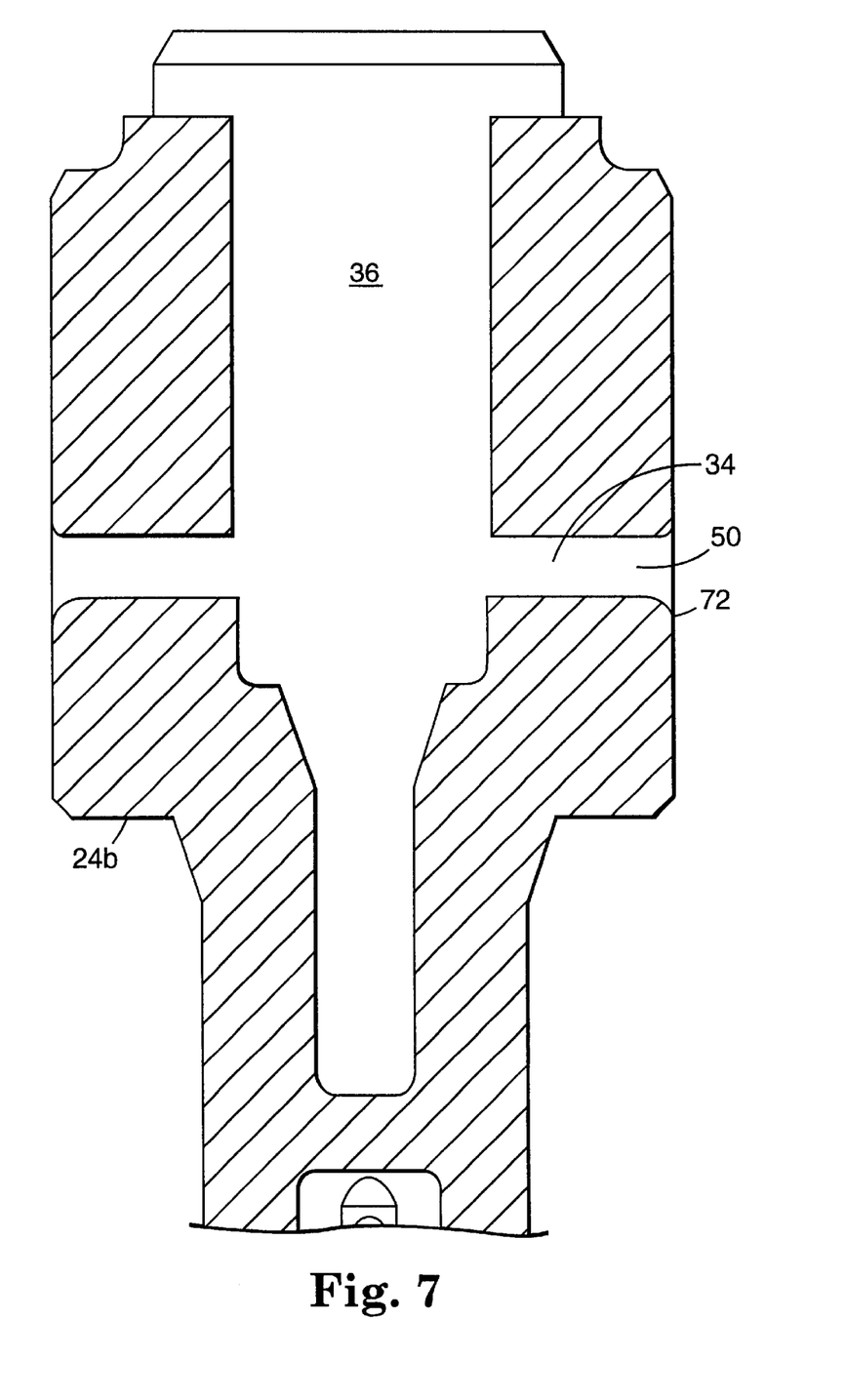
FIG. 7 is an enlarged cross-section of an alternative embodiment of the aerosol valve stem of the present invention.
Figure 8:
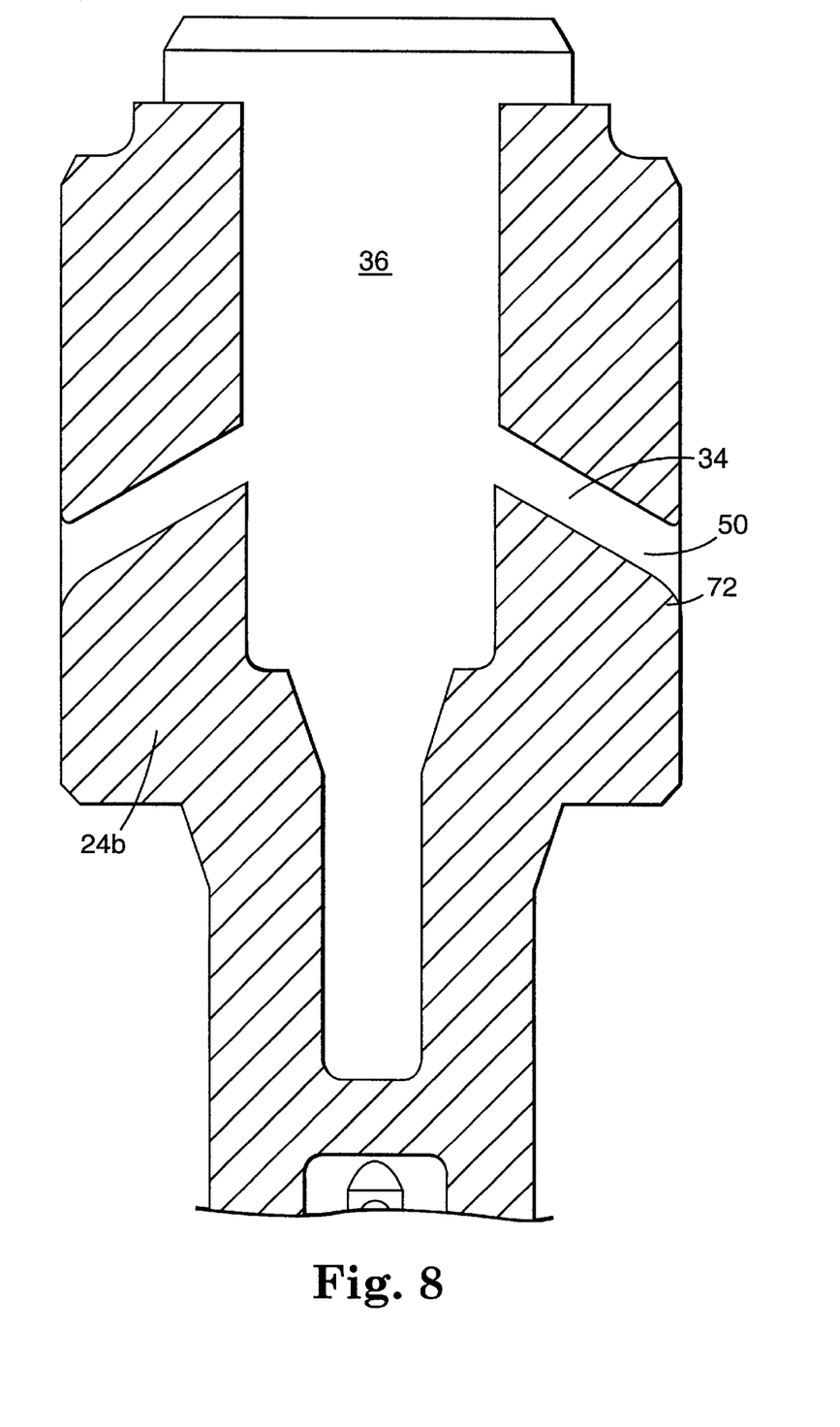
FIG. 8 is an enlarged cross-section of another alternative embodiment of the aerosol valve stem of the present invention.

The channel 34 may intersect the channel opening 50 (the channel angle) at about a 0° angle with respect to the horizontal plane of the valve stem, as shown in FIG. 7, or at an inclined angle, as shown in FIG. 8. In one embodiment, similar to that shown in FIG. 7, the channel 34 may intersect with the channel opening 50 at about a 0° angle relative to the horizontal plane of the valve stem 24 and have a channel opening 50 measuring about 0.25 mm in height and about 280° of the valve stem circumference. An alternative embodiment may have a channel opening height of about 0.5 mm.

The channel angle may range from about +90° to about −90° with respect to the horizontal plane of the valve stem. An angled channel 34 may help direct the flow formulation into the narrow annular space 32 (see FIG. 3). This, in turn, may minimize the region of low pressure that may develop as the formulation passes through the channel opening 50 and into the narrow annular space 32. Such regions of low pressure can increase the likelihood of bubble formation within the formulation. In one embodiment, similar to that shown in FIG. 8, the channel angle may be about +45° relative to the horizontal plane of the valve stem 24 and the channel opening 50 may measure about 0.25 mm in height and about 160° of the valve stem circumference. An alternative embodiment may have a channel opening height of about 0.5 mm. Any channel angle from about 0° to and including about +90°, relative to the horizontal plane of the valve stem, may be suitable for a particular application, however.

Figure 9:
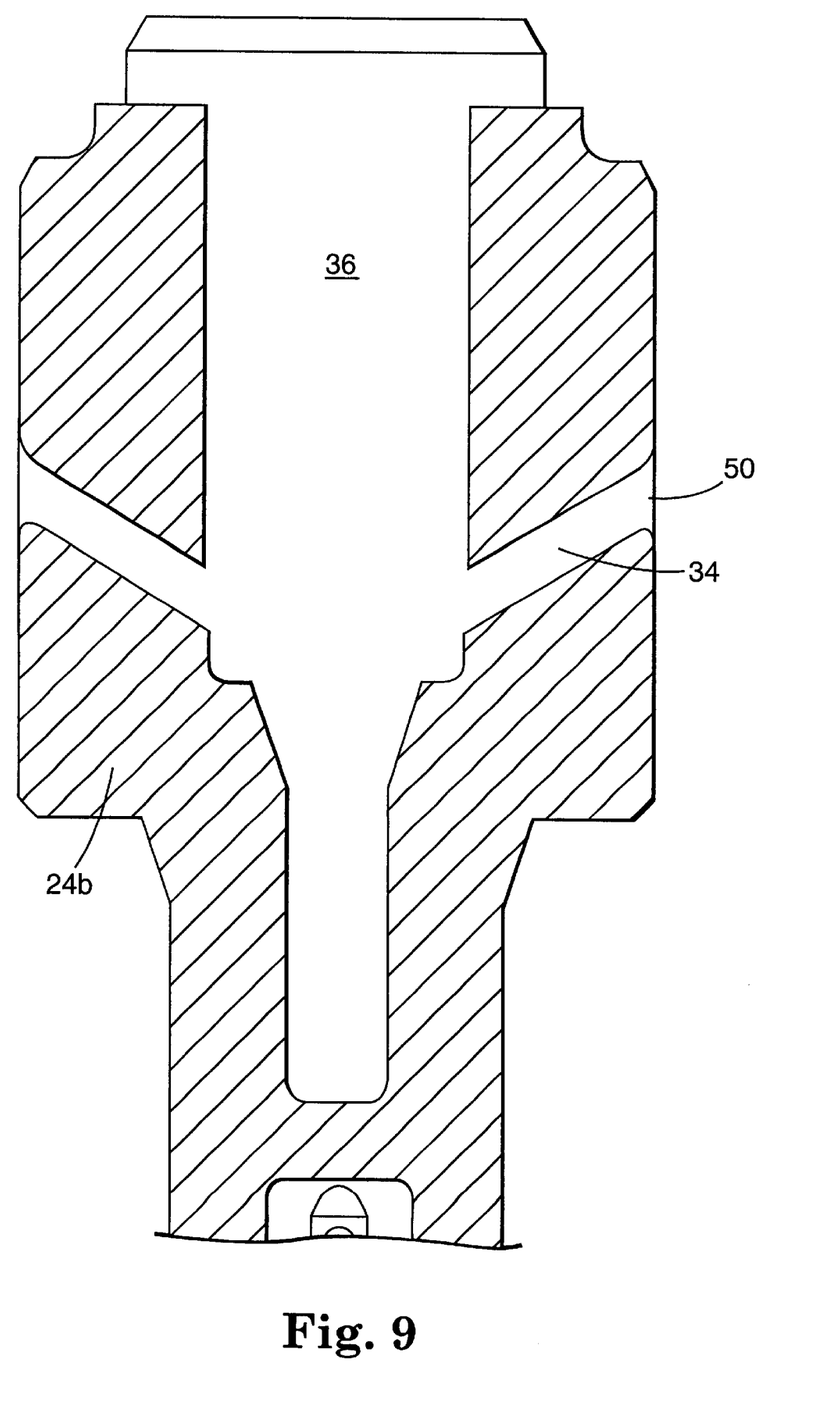
FIG. 9 is an enlarged cross-section of another alternative embodiment of the aerosol valve stem of the present invention.

In an alternative embodiment, a channel may intersect with the channel opening 50 at an angle from about 0° to about −90° with respect to the horizontal plane may be desired in certain embodiments. Such an embodiment, similar to that shown in FIG. 9, may have a channel angle of about −45° with respect to the horizontal plane of the valve stem, for example. Drug from a suspension formulation may form a sediment between dosings. In the embodiment shown in FIG. 9, such sedimented drug may preferentially collect on the floor of interior space 36, thereby reducing sedimentation of drug in the channels 34, the narrow annular space 32, or both. The sedimented drug may be more readily resuspended into the formulation from the floor of the interior space 36 than from either the channels 34 or the narrow annular space 32 when the patient shakes the inhaler. Thus, such a valve stem may promote more consistent, accurate dosing and more complete use of drugs in suspension formulations. Any channel angle from about 0° to and including about −90° may be suitable for a particular application.

In certain embodiments, one or more edges 72 of the channel opening 50 may be beveled or rounded, as shown in FIG. 7. Edges 72 modified in this way may provide a smooth transition of the flow path from the channel 34 into the narrow annular space 32. This feature also may contribute to reducing the likelihood and extent to which localized regions of low pressure will develop in the flow of formulation. Consequently, beveled or rounded edges of the channel opening 50 may help reduce the likelihood of bubble formation within the formulation.

Various modifications and alterations to this invention will become apparent to those skilled in the art without departing from the scope and spirit of this invention. It should be understood that this invention is not intended to be unduly limited by the a illustrative embodiments and examples set forth herein and that such examples and embodiments are presented by way of example only with the scope of the invention intended to be limited only by the claims set forth herein as follows.

What is claimed is:

1. An aerosol valve stem comprising:
   a body comprising a body wall defining an internal chamber;
   at least one inlet port through the body wall in fluid communication with the internal chamber;
   a channel opening in the body wall having a height and a width wherein the width is greater than the height; and
   at least one channel providing fluid communication between the internal chamber and the channel opening.

2. The aerosol valve stem of claim 1 wherein the height of the channel opening is from about 0.01 mm to about 1.0 mm.

3. The aerosol valve stem of claim 2 wherein the height of the channel opening is from about 0.1 mm to about 0.8 mm.

4. The aerosol valve stem of claim 2 wherein the height of the channel opening is about 0.25 mm.

5. The aerosol valve stem of claim 1 wherein the channel opening completely encircles the valve stem.

6. The aerosol valve stem of claim 1 wherein the channel opening comprises at least one rounded edge or at least one beveled edge.

7. The aerosol valve stem of claim 1 wherein at least one channel intersects with at least one channel opening at an angle of from about +90° to about −90° relative to a horizontal axis of the valve stem.

8. The aerosol valve stem of claim 7 wherein at least one channel intersects with at least one channel opening at an angle of from about +45° to about −45° relative to a horizontal axis of the valve stem.

9. The aerosol valve stem of claim 7 wherein at least one channel intersects with at least one channel opening at an angle of about 0° relative to a horizontal axis of the valve stem.

10. An aerosol valve stem comprising:
    a body comprising a body wall defining an internal chamber;
    at least one inlet port through the body wall in fluid communication with the internal chamber;
    a plurality of channel openings in the body wall, each channel opening having a height and a width wherein at least two channel openings define a cumulative width, and wherein the cumulative width is greater than the height; and
    at least one channel providing fluid communication between the internal chamber and each channel opening.

11. The aerosol valve stem of claim 10 wherein the height of at least one channel opening is from about 0.01 mm to about 1.0 mm.

12. A method of delivering an aerosol dose of medicine comprising:
a) providing an inhaler that comprises a valve stem comprising:
   i) a body comprising a body wall defining an internal chamber,
   ii) at least one inlet port through the body wall in fluid communication with the internal chamber,
   iii) a channel opening in the body wall having a height and a width wherein the width is greater than the height, and
   iv) at least one channel providing fluid communication between the internal chamber and the channel opening;
b) providing a formulation of aerosol medicine contained within the inhaler; and
c) actuating the inhaler.

13. A method of delivering an aerosol dose of medicine comprising:
a) providing an inhaler that comprises a valve stem comprising:
   i) a body comprising a body wall defining an internal chamber,
   ii) at least one inlet port through the body wall in fluid communication with the internal chamber,
   iii) a plurality of channel openings in the body wall, each channel opening having a height and a width wherein at least two channel openings define an cumulative width, and wherein the cumulative width is greater than the height, and
   iv) at least one channel providing fluid communication between the internal chamber and each channel opening;
b) providing a formulation of aerosol medicine contained within the inhaler; and
c) actuating the inhaler.

14. A metering valve comprising:
a housing comprising an internal chamber defined by one or more chamber walls, the internal chamber comprising an outlet aperture;
a diaphragm positioned at the outlet aperture and in sealing engagement with at least a portion of the housing;
a metering gasket in sealing engagement with one or more chamber walls;
a valve stem comprising:
   i) a body comprising a body wall defining an internal chamber,
   ii) at least one inlet port through the body wall in fluid communication with the internal chamber,
   iii) a channel opening in the body wall having a height and a width wherein the width is greater than the height, and
   iv) at least one channel providing fluid communication between the internal chamber and the channel opening,
wherein the valve stem passes through the aperture in slidable sealing engagement with both of the diaphragm and the metering gasket; and
an annular space having a width defined by a distance between the chamber wall and the valve stem.

15. The metering valve of claim 14 wherein the height of the channel opening is from about 1 to about 5 times the width of the annular space.

16. The metering valve of claim 14 wherein the height of the channel opening is about 3 times the width of the annular space.

17. The metering valve of claim 14 wherein the height of the channel opening is from about 0.01 mm to about 1.0 mm.

18. The metering valve of claim 17 wherein the height of the channel opening is from about 0.1 mm to about 0.8 mm.

19. The metering valve of claim 17 wherein the height of the channel opening is about 0.25 mm.

20. The metering valve of claim 14 wherein the channel opening completely encircles the valve stem.

21. The metering valve of claim 14 wherein the channel opening comprises at least one rounded edge or at least one beveled edge.

22. The metering valve of claim 14 wherein at least one channel intersects with at least one channel opening at an angle of from about +90° to about −90° relative to a horizontal axis of the valve stem.

23. The metering valve of claim 22 wherein at least one channel intersects with at least one channel opening at an angle of from about +45° to about −45° relative to a horizontal axis of the valve stem.

24. The metering valve of claim 22 wherein at least one channel intersects with at least one channel opening at an angle of about 0° relative to a horizontal axis of the valve stem.

25. A metering valve comprising:
a housing comprising an internal chamber defined by one or more chamber walls, the internal chamber comprising an outlet aperture;
a diaphragm positioned at the outlet aperture and in sealing engagement with at least a portion of the housing;
a metering gasket in sealing engagement with one or more chamber walls;
a valve stem comprising:
   i) a body comprising a body wall defining an internal chamber,
   ii) at least one inlet port through the body wall in fluid communication with the internal chamber,
   iii) a plurality channel openings in the body wall, each channel opening having a height and a width wherein at least two channel openings define a cumulative width, and wherein the cumulative width is greater than the height; and
   iv) at least one channel providing fluid communication between the internal chamber and each channel opening,
wherein the valve stem passes through the aperture in slidable sealing engagement with both of the diaphragm and the metering gasket; and
an annular space having a width defined by a distance between the chamber wall and the valve stem.

26. The metering valve of claim 25 wherein the height of at least one channel opening is from about 1 to about 5 times the width of the annular space.

27. The metering valve of claim 25 wherein the height of at least one channel opening is about 3 times the width of the annular space.

28. The metering valve of claim 25 wherein the height of at least one channel opening is from about 0.01 mm to about 1.0 mm.

29. The metering valve of claim 28 wherein the height of at least one channel opening is from about 0.1 mm to about 0.8 mm.

30. The metering valve of claim 28 wherein the height of at least one channel opening is about 0.25 mm.

* * * * *